United States Patent [19]

Bruhl, Jr.

[11] Patent Number: 5,004,333
[45] Date of Patent: Apr. 2, 1991

[54] INTEGRALLY FORMED TWO-PIECE EYESHIELD

[75] Inventor: Daniel E. Bruhl, Jr., Fort Worth, Tex.

[73] Assignee: Trident Medical Products, Inc., Ft. Worth, Tex.

[21] Appl. No.: 386,276

[22] Filed: Jul. 28, 1989

[51] Int. Cl.$^5$ .......................... G02C 7/16; A61F 3/00
[52] U.S. Cl. ...................................... 351/45; 128/858
[58] Field of Search ................. 351/45, 46; 128/163, 128/858

[56] References Cited

U.S. PATENT DOCUMENTS 4,850,376  7/1989  Della Vecchia et al. ........... 128/858
4,862,902  9/1989  Goffman ............................. 128/858

Primary Examiner—Paul M. Dzierzynski
Attorney, Agent, or Firm—Charles W. McHugh

[57] ABSTRACT

An eyeshield for covering an eye that is being treated for some medical problem, so as to shield the eye until such time as it has healed. The eyeshield includes a substantially firm but bendable foraminous member having a concave interior surface that is adapted to be juxtaposed with the eye—to create a kind of shallow "vault" over the eye. The preferred material for the foraminous member is a sheet of 6061 aluminum alloy having a thickness of about 0.025 inch. The member has a peripheral edge or rim having the general shape of an ellipse, with a major axis of about 3 inches and a minor axis of about 2.4 inches. The eyeshield also includes a relatively thick but lightweight border that is permanently mounted around the rim in such a way as to completely envelop the same. The thick border is preferably formed from a flexible material that has rubber-like properties, so that it may yield to any manual bending of the foraminous member that may be accomplished in order to make the member achieve a better fit with the particular bone structure of a given patient. The foraminous member has a multitude of small apertures, preferably 100 or more, that are adapted to foster ventilation of the eye and the nearby facial skin. It also has a plurality of peripheral recesses, to aid in integrally molding the border to the foraminous member. Thus, the border and foraminous member may be permanently affixed to each other—and interlocked in such a way as to prevent any relative rotation therebetween.

12 Claims, 1 Drawing Sheet

INTEGRALLY FORMED TWO-PIECE EYESHIELD

BACKGROUND OF THE INVENTION

This invention relates generally to a relatively firm eye cover that is adapted for use in the treatment of eye problems caused by disease, injury, etc.; more specifically, it relates to a mostly metal eyeshield that is adapted to shield either one of a wearer's eyes from errant contact with undesirable objects—as well as to foster wearer comfort while an eye is healing.

During the medical treatment of many kinds of eye problems, including injuries and the like, a patient is often required to wear a protective eyeshield over the eye that is healing or being treated. Obviously, the eyeshield is intended to protect the eye while it is healing without causing additional risk or discomfort for the wearer. Unfortunately, quite a few of the eyeshields that are currently being used are not only uncomfortable but they are also somewhat awkward to wear. And many of these devices are not constructed in such a way as to foster the kind of cleanliness that is preferred by medical personnel; and although many eyeshields of the prior art can be sterilized, the task of doing so is often rather time-consuming.

One such eyeshield is made from a thin piece of metal, typically aluminum about 0.027 inch thick; it is generally elliptical in shape, with its length being about three inches and its height being about two and three-eighths inches. Because its very thin edge can be felt by the sensitive area around a person's eye, and the sensation is that of skin being pressed by something that is relatively sharp, a kind of thin cloth "cushion" in the form of a narrow edge guard (somewhat like a garter) is often used to surround the periphery of the shield. Another form of peripheral "cushion" is a strip of foamed plastic tape, typically about an inch wide, that is manually folded over the edge of the metal shield before it is installed over the eye. The combination of a metal shield and some kind of attached cushion is strapped to a person's head in such a way as to securely hold the eyeshield in a fixed position over the injured eye. It will be readily apparent that with this system of eye protection, two distinct and separable pieces are required to create the total eyeshield. In terms of cleaning (or sterilizing) the eyeshield, such a two-piece system is not ideal, because the metal shield and separable cushion cannot be thoroughly cleaned as a unit. That is, a cloth edge guard or "garter" must generally be cleaned in a washing machine or the like, and then dried in a dryer, before it can be used again. Of course, the metal shield could not be conveniently cleaned in the same way; instead, a shield must generally be separately sterilized by steam autoclaving or the like. Furthermore, after the two pieces have been separately cleaned, significant manual handling of the shield in order to install a peripheral cushion can introduce the risk of again contaminating the shield—a shield that is supposed to be kept as clean as possible.

One other problem with a separable, two-piece eyeshield is that the metal shield is susceptible to being rotated inside its smooth cloth sheath; that is, when an elliptical shield is subjected to a glancing blow, there is nothing to prevent the shield from becoming repositioned so as to allow its edge to escape the cloth sheath in such a way as to cause wearer discomfort or injury. Furthermore, if such a metal eyeshield were accidentally pushed forcefully against the wearer's face, it is questionable that a thin cloth sheath could provide enough protection to preclude the sharp metal rim from pressing uncomfortably against or causing injury to the wearer's flesh.

Another eyeshield that is sometimes used in the treatment of eye injuries is referred to as the "Universal Eye Shield." It is made of a rigid polycarbonate material and is available from Trident Medical Products Inc. of Fort Worth, Texas. Although this type of eyeshield (having a thickness of about 0.065 inch) may be used without peripheral cushions or the like, it has not found widespread acceptance—apparently because it cannot be bent or manipulated in order to make it conform to the individual bone structure of the patient who is to wear it. And a rigid, plastic eyeshield is considered by some persons to be uncomfortable if it does not provide a peripheral structure that is adapted to flex so that it can be shaped to bear gently against the soft and supple flesh around the eye.

An additional problem with a polycarbonate (or other rigid plastic) eyeshield is that it will sometimes tend to slide with respect to the skin around a person's eye—when subjected to lateral loads. When compared to materials such as soft rubber, the relatively low coefficient of friction between the hard plastic material and the smooth (and often oily) facial skin that surrounds an eye would not effectively tend to inhibit sideward movement of the eyeshield over the skin. Under sideward impact, such an eyeshield might readily slip over the wearer's skin and fail to remain in place where it is supposed to protect the wearer's eye.

While the above-described eyeshields might be useful in the treatment of some eye problems, it seems that the designers of these prior art eyeshields have neglected the importance of easy sterilization or cleaning, as well as wearer comfort. Accordingly, there has remained a need for a unitary eyeshield which may be conveniently and thoroughly sterilized without disassembly, and which also has a border that is adapted to lie directly—and more comfortably—against the skin surrounding an eye. It is an object of this invention to provide such a protective eyeshield.

Another object is to provide a unitary and integrally formed eyeshield that is made from two different materials: one material being adapted to provide a suitable compromise between rigidity (for protecting the eye) and moldability (for matching the geometry of the face), and the second material being adapted to provide an adequately soft border to make comfortable contact with the wearer's face, while not comprising hygiene.

It is a further object to provide a protective eyeshield that is formed from two pieces that are permanently interlocked in such a way that they cannot be moved relative to each other, either deliberately or accidently.

Still a further object is to provide a two-piece eyeshield that is integrally formed in such a way that the seams between the two pieces are essentially gapless, so as to foster sanitation by minimizing the possibility of accumulating significant quantities of dirt, debris, facial oils, etc., on the eyeshield.

Another object is to provide a protective eyeshield having a border (i.e., a face-to-shield interface) that may be contoured and configured so as to lie in intimate contact with the facial area surrounding an eye, said border being formed from a material having a coefficient of friction that inhibits unwanted sliding movement of the eyeshield over the wearer's skin.

BRIEF DESCRIPTION OF THE INVENTION

Figure 1:
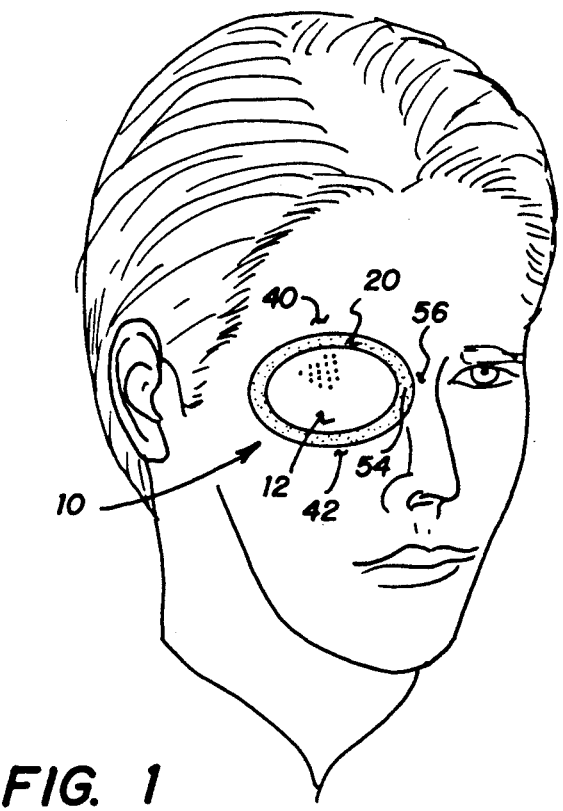
FIG. 1 is a perspective view of a person's head illustrating a protective eyeshield as it might appear when positioned over an eye (but omitting—for clarity—any bandage materials that would be required to hold the eyeshield in position)

In brief, the invention relates to an eyeshield that is particularly useful for covering an eye that is being treated for some medical problem, so as to shield it from unwanted contact with errant bodies until such time as the eye has healed. The shield may be securely held in position over the injured eye in a conventional manner by gauze strips or other traditional bandage materials. And the eyeshield is advantageously configured so that its periphery may be safely and comfortably placed in direct contact with the wearer's skin—thereby eliminating the need for any auxiliary "cushioning" in the form of tape strips or cloth sheaths or the like.

The eyeshield includes a substantially firm but bendable foraminous member having a concave interior surface that is adapted to be juxtaposed with the eye—to create a kind of shallow "vault" over the eye. The preferred material for the foraminous member is a sheet of 6061 aluminum alloy having a thickness of about 0.025 inch. The foraminous member has a peripheral edge or rim having the general shape of an ellipse, with a major axis of about 3 inches and a minor axis of about 2.4 inches. The member is ideally sized to cover the eye as well as a small portion of the facial area immediately surrounding the eye. The foraminous member is symmetrical about both its major and minor axes, so that the eyeshield may be used on either the right or left eye. The eyeshield also includes a relatively thick but lightweight border that is permanently mounted around the rim in such a way as to completely envelop the same. The thick border is preferably formed from a flexible material that has rubber-like properties, so that it may yield to any manual bending of the foraminous member that may be accomplished in order to make the member achieve a better fit with the particular bone structure of a given patient. Thus, the border serves as a permanent interfacing structure between the thin (and therefore potentially sharp-edged) foraminous member and the tender skin that typically surrounds the eye.

The foraminous member has a multitude of small apertures that are adapted to foster ventilation of the eye and the nearby facial skin; the small apertures also improve the ability of the eye to focus on things in the field of view. Looking through small holes in an opaque member reduces any existing refraction error of the eye, which has a psychologically beneficial effect on the person wearing the eyeshield. The foraminous member also has a plurality of peripheral recesses that are spaced around it, to aid in integrally molding the border to the foraminous member. With such a construction, the border and foraminous member are permanently affixed to each other—and interlocked in such a way as to prevent any relative rotation therebetween. By integrally molding the border to the foraminous member with injection molding equipment or the like, a unitary eyeshield is created. And by the judicious selection of the material for the border, a metallic foraminous member and a resilient border may be conveniently cleaned as a unit and then immediately placed back in an operative position over an eye, without the need for any re-assembly.

DETAILED DESCRIPTION OF A PREFERRED EMBODIMENT OF THE INVENTION

Figure 2:
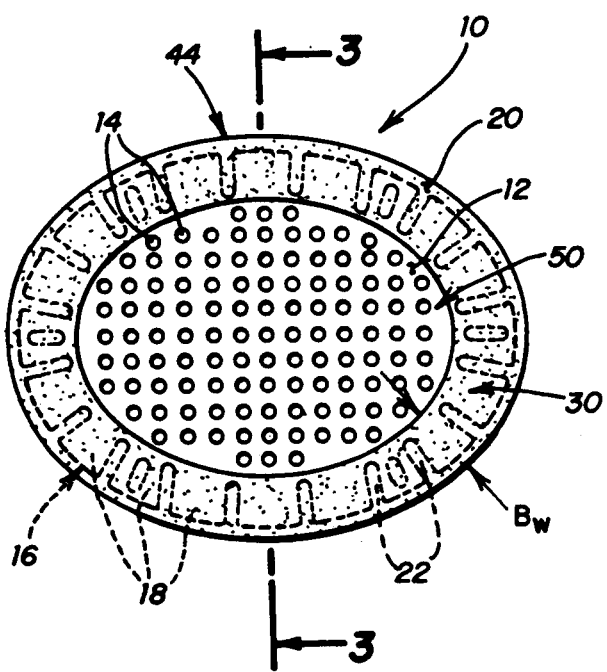
FIG. 2 is a front elevational view of the eyeshield showing the relatively thick border member permanently connected to a foraminous member, and showing by broken lines the plurality of peripheral recesses that contribute to the effective locking of the border to the foraminous member.

Referring initially to FIGS. 1 and 2, a protective eyeshield 10 is shown as it might appear when positioned so as to cover a person's eye. The eyeshield 10 is particularly well suited for covering an injured eye after the eye has been medically treated so as to protect the eye from errant contact with undesirable things while it is healing. Of course, it should be recognized that the invention could also be used as a general-purpose eyeshield for humans, animals, etc. For simplicity herein, the eye being covered will be referred to as the injured eye, regardless of why the eye is considered to be in need of treatment or why it is being covered. Suitable straps or gauze bandages are, of course, used to hold the eyeshield 10 in position over the patient's eye, but they form no part of this invention and they have been omitted in FIG. 1 for the sake of clarity.

The eyeshield 10 preferably includes a relatively thin (i.e., 0.025 inch) but substantially firm and foraminous member 12 having a concave interior surface adapted to be juxtaposed with the injured eye. The foraminous member 12 has a plurality of discrete apertures 14 of a sufficient quantity and size as to foster ventilation of the eye and the facial area immediately surrounding said eye. A suitable quantity of apertures has been found to be about 100 or so, each having a diameter of about 0.10 inch. The foraminous member 12 has a peripheral edge 16 (shown by a segmented line in FIG. 2) that may be considered to be formed by a series of generally curved segments 18. A relatively thick border member 20 is mounted around the peripheral edge 16 of member 12 so as to completely envelop the same. The border member 20 is preferably formed in such a way as to be permanently affixed to member 12. For example, the foraminous member 12 may be stamped from an elongated strip of relatively soft aluminum about 0.025 inch thick, using a progressive series of hard metal dies; 6061 alloy aluminum is a suitable material, if it is subsequently hardened to essentially a T-6 condition. After completely shaping and hardening the member 12, it may be cleaned and placed in a mold so that a suitable border 20 can be cast or molded therearound.

In the preferred embodiment of the invention, the border material is hypoallergenic and of a "medical grade" quality, and it has physical characteristics such that it may be molded like a thermoplastic material. A suitable material is available from Monsanto Chemical Company of St. Louis, Mo., under the designation of Santoprene thermoplastic rubber. Santoprene rubber is described by the manufacturer as a biocompatible material having non-toxic properties; it is also adapted to retain its non-toxic properties after being sterilized by conventional methods. Such sterilizing methods include steam autoclaving, high energy radiation, and ethylene oxide exposure. With the construction described here, the border member 20 as well as the aluminum foraminous member 12 can withstand conventional steam sterilization up to a temperature of about 240 degrees Fahrenheit. Thus, a person may conveniently sanitize the eyeshield 10 in a home (in boiling water) or hospital environment without special handling.

Another feature about the eyeshield 10 that facilitates sterilization and enhances cleanliness arises from the way in which the eyeshield is formed. After the border material has been heated in an injection molding machine and then molded around the member 12, the material will shrink as it solidifies—so as to form circumferential seams 50, 52 between the border 20 and member 12 that may be accurately classified as gapless. With no gap for contaminants to become trapped in, such contaminants are positively prevented from accumulating between the members 20, 12; and cleanliness of the eyeshield is enhanced throughout its useful life.

Spaced circumferentially around the foraminous member 12 are a plurality of recesses 22, with the border member 20 having a size that is adequate to completely overlap said recesses. A length for the border 20 of about three-eighths inch (as measured in a direction that is generally radial and parallel to the adjacent surface of the member 12) will usually be adequate to cover all of the recesses. When the border member 20 is molded around the foraminous member 12 so as to be integrally connected therewith, the material of member 20 will permeate the recesses 22 in order to positively prevent any relative rotation between the two members 12, 20. The resulting integral, unitary structure may be cleaned and sterilized as a "single" piece—and then returned to use by the wearer without the need for any re-assembly.

Figure 3:
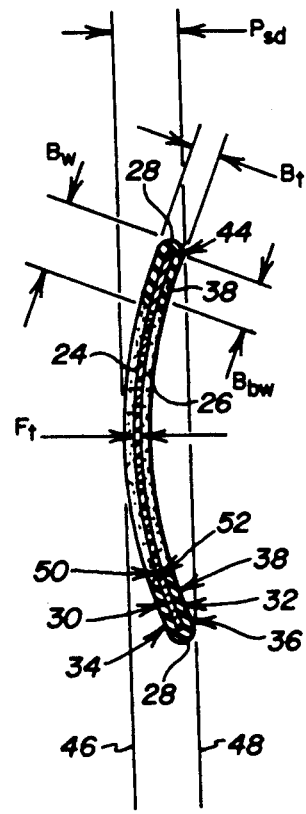
FIG. 3 is a cross-sectional side view of the eyeshield (in the plane represented by the lines 3—3 in FIG. 2), and showing the relative thicknesses of the foraminous member and the border member, and also showing the rounded outer edge of the border member.

Referring additionally to FIG. 3, the foraminous member 12 may be said to have a mean thickness as measured from its frontal (and exterior) surface 24 to its rearward (and interior) surface 26. This mean thickness is identified by the notation $F_t$ in FIG. 3, and is ideally about 0.025 inch. When the member 12 of this thickness is formed of lightweight but hardened aluminum, it will be rigid enough to resist deflection when subjected to unplanned loading due to the ordinary bumps and knocks of everyday living (as when the wearer unexpectedly bumps into an open cabinet door); but it will still have enough malleability to be slowly and carefully shaped by a physician in order to conform to the bony orbital rim surrounding the wearer's eye. The preferred material for the border member 20 is also capable of being slightly twisted—as required—to meet almost any facial configuration that is encountered by a physician. The preferred Santoprene material has a Shore durometer hardness within the range of about 55 to 64, which is hard enough to provide an adequate amount of protection to the wearer's skin as a result of an unexpected blow. That is, unlike peripheral cloth "sheaths" of the prior art, a border made of Santoprene rubber (or its equivalent) is tough enough so that it will tend to absorb and distribute the kinetic energy of a blow over a wide area of a wearer's skin, instead of simply passing the force of a blow straight through to a localized spot near the eye. On the other hand, the border material disclosed herein is not so hard as to cause damage to the wearer's skin as a result of a modest blow imparted to the front of the foraminous member 12.

It also should be recognized that the average thickness of the border 20 (about 0.10 inch) is substantially greater than the mean thickness of the foraminous member 12 (about 0.025 inch); the border thickness is represented by the designation $B_t$ and its width by the notation $B_w$ in FIG. 3. The border 20 also has a rounded outer edge 28, with a preferred radius of about 0.04 inch. Naturally, the combination of the border's thickness and its gently rounded edge 28 makes the eyeshield 10 more comfortable to wear against the facial skin surrounding an injured eye.

The border 20 is configured to wrap around the peripheral edge 16 of rigid member 12 in such a way as to cover circumferentially extending bands 30, 32 in the member 12 around both its exterior surface 24 and interior surface 26. A frontal portion 34 of the border 20 lies adjacent the exterior band 30 of member 12, and a rearward portion 36 of the border lies adjacent the interior band 32 of member 12; both border portions 34, 36 have substantially equal thicknesses. The border 20 has a rearwardly facing and circumferentially extending band-like support surface 38 that preferably has a width of at least ¼ inch (indicated by the notation $B_{bw}$ in FIG. 3). The band-like support surface 38 is generally smooth and flat, so that it may lie directly against the skin of the forehead 40 and cheek 42 around an injured eye. It should be appreciated that the combination of a large band circumference and a wide band configuration permits the weight of the eyeshield 10 to be distributed over a wide portion of skin surrounding the injured eye so as to foster wearer comfort.

To further promote comfort and protection for the wearer, the entire eyeshield 10 has a concave shape, with the result that both the border member 20 and the peripheral edge 16 of rigid member 12 are gently curved rearwardly. In this way, an upper arcuate portion 44 of the band-like support surface 38 may be positioned so as to securely rest on top of the bony orbital rim (over the eye and adjacent the eyebrow), such that the eyeshield 10 may be considered to be at least partially supported by the brow. Likewise, the lateral and interior orbital rim and the zygomatic arch provide bony support for the portion of the eyeshield that overlies these structures. Medially, the eyeshield is supported by the bridge of the nose. In this manner the shield can be expected to transfer the force of a direct blow to these bony structures, thereby reducing the risk of injury to the eye. Additionally, the eyeshield 10 has a profile that is sufficiently thin so that it will not protrude substantially away from the face of the wearer when the eyeshield has been installed; this permits the wearer to wear his or her conventional glasses over the eyeshield, to either correct a visual deficiency in the uninjured eye, or to shade the eyes from bright sunlight, or both. This thin profile is represented by the separation distance between a pair of parallel planes 46, 48 that pass respectively through the most frontal and the most rearward elements of the eyeshield 10. The separation distance is preferably not appreciably greater than about 0.4 inch, as represented by the notation $P_{sd}$ in FIG. 3. With the terms "frontal" and "rearward" in mind, it should be pointed out that these terms are being used herein as if a person had already positioned the eyeshield so that it is juxtaposed with his or her orbital rim, and as if the person were standing erect and "at attention." Thus, any references herein to directions (e.g., frontal or rearward, up or down, interior or exterior, etc.) are employed as they might be used by the person wearing the eyeshield.

While the preferred profile of the eyeshield 10 is relatively thin, it must not be so thin as to eliminate the "vaulting" effect that is desirable in order to provide adequate ventilation and protection for the eye, and to provide clearance for the wearer's eyelashes. It will surely be appreciated that a protective eyeshield would be rather uncomfortable to wear if it were so close to the covered eye as to cause eyelashes to drag on an interior surface of the shield every time the wearer blinked or closed his or her eyes.

It should be clear that the unique eyeshield 10 described herein provides a variety of advantageous "human engineering" features, such as the relatively firm but still cushion-like border 20 that serves as an interface structure between the rigid member 12 and the wearer's supple skin. Also, the two members 12, 20 are consolidated into a unitary construction to make it easier for a person to both handle and clean the eyeshield 10. Another advantageous feature of the eyeshield 10 is that the rubber-like material of the "interface" border 20 is sufficiently flexible as to be conformable to the wearer's skin; and the rubber-like material is adapted to inhibit the eyeshield from slipping or sliding with respect to the wearer's skin. This is because the coefficient of friction between the rubber-like border material and normal facial skin is substantially higher than the coefficient of friction of hard, polycarbonate plastic materials that have been used in other eyeshields. With such a construction, the border 20 will more readily "hug" the wearer's facial skin and remain in its initially placed position next to the eye. Furthermore, the border 20 will tolerate any conventional sterilizing techniques, including the use of steam, gas, gamma rays, etc.

In use, the eyeshield 10 is positioned (as shown in FIG. 1) so that it is juxtaposed with the injured eye, with the upper arcuate portion 44 of the border 20 overlying the eyebrow or forehead 40 above the eye. Of course, another way of explaining the positioning of the eyeshield 10 is to describe it as "vaulting" the injured eye. The eyeshield 10 may be slightly rotated until an inner curved portion 54 of the border 20 is snugly nestled against the curved facial area formed by the brow 40 and the upper portion 56 of the nose. If the eyeshield 10 does not fit a patient's skull exactly, it may be grasped in the hands and bent without too much trouble—until it reaches the stage of being equivalent to a custom-made shield. Bandage materials (not shown) may be used with a clean eyeshield 10 to securely hold the the eyeshield in position around the eye. When it is desirable to clean the eyeshield 10, the entire unit may be washed with soap and water, or conveniently subjected to steam autoclaving, ethylene oxide gas, or gamma irradiation (or its equivalent) for sterilization.

While only a preferred embodiment of the invention has been disclosed herein, it should be apparent to those skilled in the art that modifications can be made without departing from the spirit of the invention. For example, the border member could be "custom" formed so as to more readily conform to the curved contour of the forehead and nose of a particular patient. This might minimize any fitting time when the eyeshield is being initially shaped for a new patient, and it could make the eyeshield even more comfortable to wear. Also, a lower arcuate portion of the band-like surface of the border could be slightly flared forward so that it would more readily lie against the cheek of the wearer, and more evenly distribute the weight of the eyeshield over the cheek. Additionally, there are some manufacturers who consider Santoprene thermoplastic rubber to be somewhat difficult to mold in thin sections. For those who wish to avoid the use of Santoprene, there are other materials that have similar physical properties, including medical-grade PVC resins, such as Teknor Apex PVC, etc. Thus, any structure or material shown herein is intended to be exemplary and is not meant to be limiting, except as described in the claims appended hereto.

What is claimed is:

1. An eyeshield adapted to cover a person's eye after the eye has been medically treated, such that the eye might be physically protected while the eye is healing, comprising:
   a. a relatively thin but substantially firm and foraminous member having a concave interior surface adapted to be juxtaposed with a person's eye so as to vault the eye and shield it from contact with errant bodies until such time as the eye has healed, and said foraminous member having a thickness as measured from its frontal and exterior surface to its rearward and interior surface, and also having a peripheral edge formed from generally curved segments, and said foraminous member having a plurality of discrete apertures of a sufficient quantity and size as to foster sight and to foster ventilation of both the eye and the facial area immediately surrounding said eye; and
   b. a relatively thick border member mounted around the peripheral edge of said foraminous member so as to envelop the same, said border member being integrally molded in contact with said foraminous member so as to be permanently affixed thereto, and said border member having an average thickness that is substantially greater than the average thickness of said foraminous member, and the border member being significantly softer than the foraminous member.

2. The eyeshield as claimed in claim 1 wherein the plurality of apertures includes at least 100 apertures, and said apertures have an average size of about 0.1 inch.

3. The eyeshield as claimed in claim 1 wherein said foraminous member has a plurality of recesses spaced circumferentially around said member, and said border member completely envelops said recesses, and wherein any two adjacent recesses form an acute angle with respect to one another, and wherein said border member is integrally molded around said foraminous member in such a way as to permeate the recesses, whereby any relative rotation between said border member and said foraminous member is absolutely precluded.

4. The eyeshield as claimed in claim 1 wherein the material from which the border member is made is injection molded about said foraminous member so as to form an integral unitary structure, whereby the entire eyeshield may be cleaned as a unit and returned to service without the need for any reassembly.

5. The eyeshield as claimed in claim 1 wherein said border member is formed from a rubber-like material having physical characteristics such that it may be molded like a thermoplastic material.

6. The eyeshield as claimed in claim 1 wherein said foraminous member is formed from soft aluminum alloy having a thickness of about 0.025 inch, and said aluminum being hardenable to a hardness of at least T-6, whereby said foraminous member may resist distortion when experiencing undesirable compressive and tensile loads.

7. The eyeshield as claimed in claim 1 wherein said border member has a Shore durometer hardness within the range of about 55 to 64, whereby said border member is sufficiently rigid as to help inhibit unwanted flexure of said foraminous member.

8. The eyeshield as claimed in claim 1 wherein the border member is about ⅜ inch wide around the entire circumference of the eyeshield.

9. The eyeshield as claimed in claim 1 wherein the border member has a circumferentially extending band-like support surface having a width of at least ¼ inch, said band-like support surface being generally smooth and flat, and facing rearwardly so that it may lie directly against the skin of the forehead and cheek around an injured eye, whereby the weight of the eyeshield may be distributed over the facial area surrounding the injured eye to foster comfort.

10. The eyeshield as claimed in claim 1 wherein said border member is formed from a medical-grade rubber material having non-toxic and hypoallergenic properties, and wherein said rubber material is stable and retains its non-toxic properties after being sterilized by conventional methods selected from the group comprising steam autoclaving, high energy radiation, and ethylene oxide exposure.

11. The eyeshield as claimed in claim 1 wherein the border member is formed from a thermoplastic rubber, and wherein said foraminous member is formed from 6061 aluminum alloy such that the eyeshield can withstand conventional steam sterilization up to a temperature of about 240 degrees Fahrenheit, whereby a person may conveniently sterilize the eyeshield in a home by immersing it in boiling water.

12. The eyeshield as claimed in claim 1 wherein said border member material is injection molded about the peripheral edge of said foraminous member, and wherein the border member material is adapted to shrink as it solidifies around said peripheral edge so as to form gapless circumferential seams between the border member and the foraminous member, whereby contaminants will be prevented from accumulating between the members, and whereby cleanliness will be enhanced.

* * * * *